United States Patent
Yamada et al.

(10) Patent No.: US 7,501,153 B2
(45) Date of Patent: Mar. 10, 2009

(54) ALKOXIDE COMPOUND, THIN FILM-FORMING MATERIAL AND METHOD FOR FORMING THIN FILM

(75) Inventors: Naoki Yamada, Tokyo (JP); Atsushi Sakurai, Tokyo (JP)

(73) Assignee: Adeka Corporation, Tokyo (JP)

( * ) Notice: Subject to any disclaimer, the term of this patent is extended or adjusted under 35 U.S.C. 154(b) by 174 days.

(21) Appl. No.: 11/665,833

(22) PCT Filed: Oct. 5, 2005

(86) PCT No.: PCT/JP2005/018445

§ 371 (c)(1),
(2), (4) Date: Apr. 20, 2007

(87) PCT Pub. No.: WO2006/043418

PCT Pub. Date: Apr. 27, 2006

(65) Prior Publication Data

US 2008/0085365 A1    Apr. 10, 2008

(30) Foreign Application Priority Data

Oct. 21, 2004 (JP) ............................. 2004-306777
Nov. 29, 2004 (JP) ............................. 2004-343513

(51) Int. Cl.
*C23C 16/00* (2006.01)
*C09D 1/00* (2006.01)

(52) U.S. Cl. .................. 427/248.1; 427/255.28; 106/287.18; 106/286.3

(58) Field of Classification Search ............. 427/248.1, 427/255.28
See application file for complete search history.

(56) References Cited

U.S. PATENT DOCUMENTS 5,932,281 A * 8/1999 Hochido et al. .......... 427/126.3
6,274,195 B1   8/2001 Rhee et al.
6,303,391 B1 * 10/2001 Hintermaier et al. ........... 438/3
6,887,523 B2 * 5/2005 Zhuang et al. ......... 427/255.31

FOREIGN PATENT DOCUMENTS

| JP | 6-321824 | 11/1994 |
|---|---|---|
| JP | 2000-351784 | 12/2000 |
| JP | 2003-119171 | 4/2003 |
| JP | 2004-27337 | 1/2004 |

OTHER PUBLICATIONS

Anwander, R. et al., Volatile Donor-Functionalized Alkoxy Derivatives of Lutetium and Their Structural Characterization, *Inorganic Chemistry*, vol. 36, No. 16, 1997, pp. 3545-3552.
Pinkas, J. et al., "Syntheses, Structures, and Thermal Behavior of Cu(hfacac) Complexes Derived from Ethanolamines", *Inorganic Chemistry*, vol. 36, No. 14, 1997, pp. 2930-2937.

* cited by examiner

*Primary Examiner*—Shamim Ahmed
(74) *Attorney, Agent, or Firm*—Young & Thompson

(57) ABSTRACT

The alkoxide compound of the present invention is represented by general formula (I) below. The alkoxide compound of the present invention is an iron compound that can be delivered in a liquid state and is easily vaporized due to its high vapor pressure. The compound particularly enables production of thin films with excellent composition controllability, and hence is suitable for producing multi-component thin films by CVD.

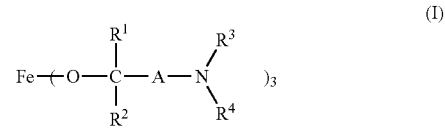

(In the formula, $R^1$ and $R^2$ each independently represent a hydrogen atom or $C_{1-4}$ alkyl group, $R^3$ and $R^4$ each represent a $C_{1-4}$ alkyl group, and A represents a $C_{1-8}$ alkanediyl group.)

13 Claims, 1 Drawing Sheet

[Fig. 1]
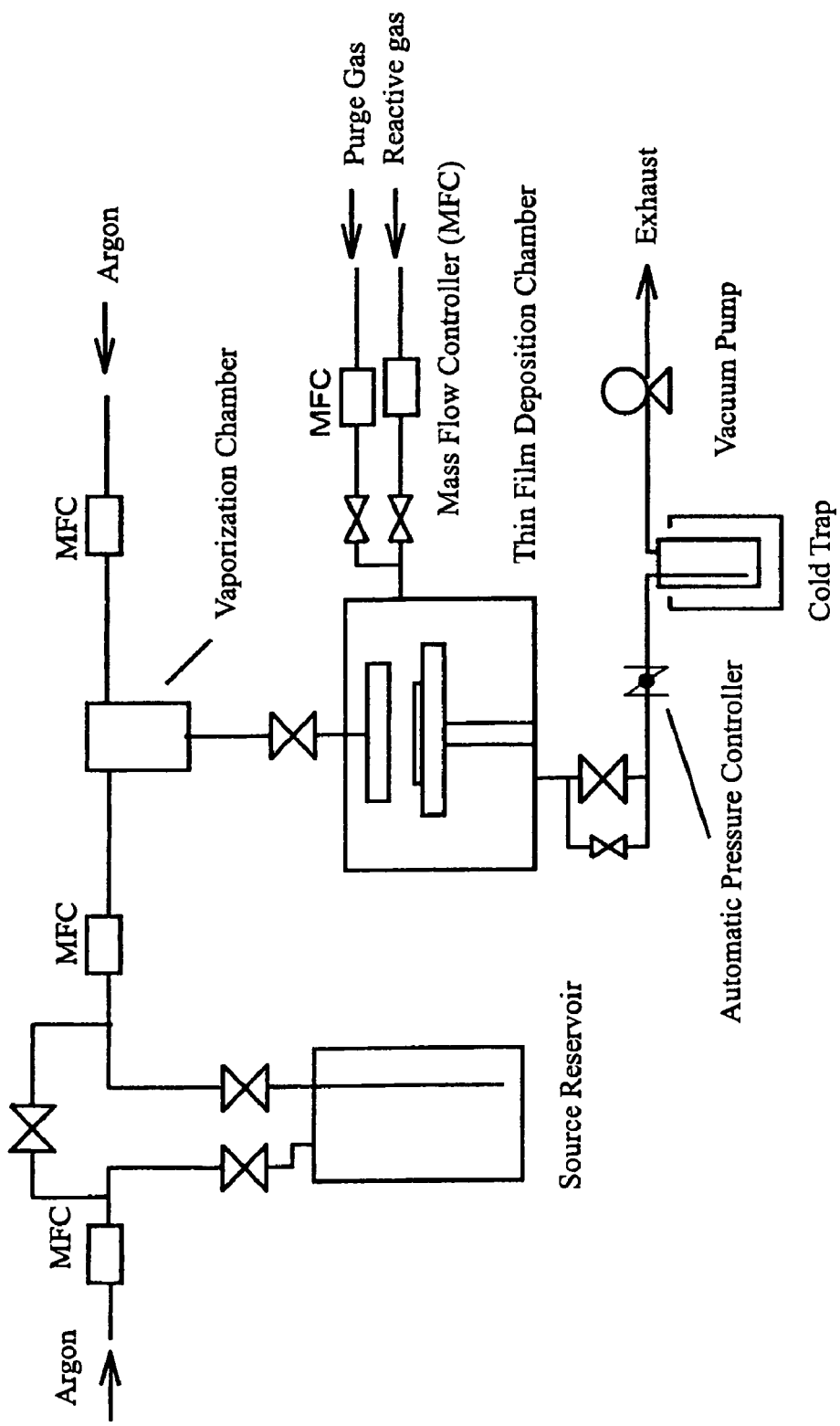

ALKOXIDE COMPOUND, THIN FILM-FORMING MATERIAL AND METHOD FOR FORMING THIN FILM

TECHNICAL FIELD

The present invention relates to a novel metal compound (an iron compound) having a ligand derived from a specific aminoalcohol, a thin film-forming material comprising the metal compound, and a method for forming iron-containing thin films using the thin film-forming material.

BACKGROUND ART

Iron-containing thin films are mainly used as members of electronic components such as high dielectric capacitors, ferroelectric capacitors, gate insulators, and barrier films and magnetic bodies.

Methods for producing the above-mentioned thin films include flame deposition, sputtering, ion-plating, MOD processes such as coating thermal decomposition, sol-gel process and the like, chemical vapor deposition (hereinafter, may be simply described as CVD), and others. The optimum production process is chemical vapor deposition including ALD (Atomic Layer Deposition) because it has a number of advantages such as excellent performances in composition control and step-coverage, suitability for mass production, and capability of hybrid integration.

In MOD and CVD processes, compounds using organic ligands are used as precursors supplying metal to thin films. As the organic ligand, there has been reported an alcohol having an ether group or a dialkylamino group at the terminal, which provides a precursor with relatively high vapor pressure and hence is suitable for forming thin films by CVD. As for silicon, Patent Document 1 reports a silicon alkoxide containing a ligand derived from an alcohol having a terminal alkoxy group. There have been also reported various metal compounds containing ligands derived from alcohols having a terminal amino group, which is a donor group coordinating to a metal atom. Patent Document 2 and Patent Document 3 report titanium compounds and zirconium compounds, Non-patent Document 1 reports lanthanide compounds, and Non-patent Document 2 reports copper aminoalkoxide compounds.

As for iron, however, there is no report on an alkoxide compound having a terminal amino group or no report on evaluation of the method for forming thin films using such a compound.

Patent Document 1: Japanese Patent Laid-Open Publication No. H6-321824
Patent Document 2: Japanese Patent Laid-Open Publication No. 2000-351784
Patent Document 3: Japanese Patent Laid-Open Publication No. 2003-119171
Non-Patent Document 1: Inorganic Chemistry, Vol. 36, No. 16, 1997, p. 3545-3552
Non-Patent Document 2: Inorganic Chemistry, Vol. 36, No. 14, 1997, p. 2930-2937

DISCLOSURE OF THE INVENTION

Problems to be Solved by the Invention

In processes for producing thin films in which a thin film is formed by vaporizing a compound, such as CVD processes, the properties demanded for a compound used as a source material (precursor) are that it is a liquid or has a melting point low enough to allow delivery in a liquid state and that it has a high vapor pressure to ensure easy vaporization. When used for producing multi-component thin films, it is also required that each precursor is not deteriorated by ligand exchange or other chemical reactions in mixing with (an)other precursor(s) or in storage and that the thermal and/or oxidative decomposition behavior during the thin film deposition is similar to that of the other precursor(s) simultaneously used. As for iron, there has been no compound that is fully satisfactory with respect to these points.

Means to Solve the Problems

The present inventors have found, as a result of many studies, that the above problems can be solved with an iron-containing alkoxide compound in which a ligand derived from a particular aminoalcohol is used and achieved the present invention.

Namely, the present invention is to provide an alkoxide compound represented by general formula (I) below, a thin film-forming material comprising the alkoxide compound, and a method for forming thin films in which vapor containing the alkoxide compound obtained by vaporizing the thin film-forming material is introduced on a substrate, followed by decomposition and/or chemical reaction of the vapor to form a thin film on the substrate.

[Formula I]

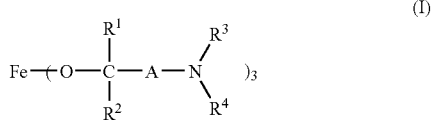

(In the formula, $R^1$ and $R^2$ each independently represent a hydrogen atom or $C_{1-4}$ alkyl group, $R^3$ and $R^4$ each represent a $C_{1-4}$ alkyl group, and A represents a $C_{1-8}$ alkanediyl group.)

BRIEF DESCRIPTION OF DRAWINGS

FIG. 1 is a schematic view showing an example of a CVD apparatus used in the thin film-formation method of the present invention.

BEST MODE FOR CARRYING OUT THE INVENTION

The alkoxide compound of the present invention is represented by general formula (I) and particularly suitable as a precursor in thin film-formation methods involving a vaporization step such as CVD including ALD.

The alkoxide compound of the present invention represented by general formula (I) is more liable to decomposition induced by heat and/or oxygen but more stable to chemical reactions than known iron alkoxide compounds. This fact means that when used alone, the alkoxide compound is energetically advantageous in thin film-formation processes, and that when used in combination with (an)other precursor(s), it is advantageous in controlling compositions of thin films because the decomposition behavior can be easily adjusted to be appropriate and also advantageous in operation because, for example, the compound may be used as a mixture with the other precursor(s).

In general formula (I), the $C_{1-4}$ alkyl group represented by $R^1$, $R^2$, $R^3$, or $R^4$ includes methyl, ethyl, propyl, isopropyl, butyl, sec-butyl, tert-butyl, and isobutyl. The alkanediyl group represented by A may be linear or may have one or more branches at any position so far as the total number of carbon atoms is 1 to 8. The alkanediyl group represented by A is preferably a group forming an energetically stable 5- or 6-membered ring when the terminal dialkylamino group, which is a donor group, is coordinated to an iron atom. Preferred alkanediyl groups include groups represented by general formula (II) below. The alkoxide compound of the present invention may have an optical isomer but both the enantiomers should not be differentiated.

[Formula 2]

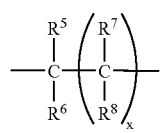

(II)

(In the formula, $R^5$ to $R^8$ each independently represent a hydrogen atom or a $C_{1-4}$ alkyl group, x represents 0 or 1, and the total number of carbon atoms in the group represented by the formula is 1 to 8.)

When the terminal donor group in the ligand is coordinated to the iron atom to form a cyclic structure, the alkoxide compound of the present invention is represented by general formula (III) below. The alkoxide compound of the present invention, even though representatively given by general formula (I) above, is not differentiated from the alkoxide compound given by general formula (III), and conceptually includes both of them.

[Formula 3]

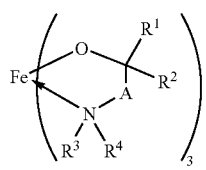

(III)

(In the formula, $R^1$ and $R^2$ each independently represent a hydrogen atom or $C_{1-4}$ alkyl group, $R^3$ and $R^4$ each represent a $C_{1-4}$ alkyl group, and A represents a $C_{1-8}$ alkanediyl group.)

Specific examples of the alkoxide compound of the present invention include Compounds 1 to 15 below.

[Formula 4]

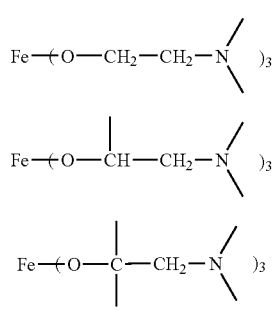

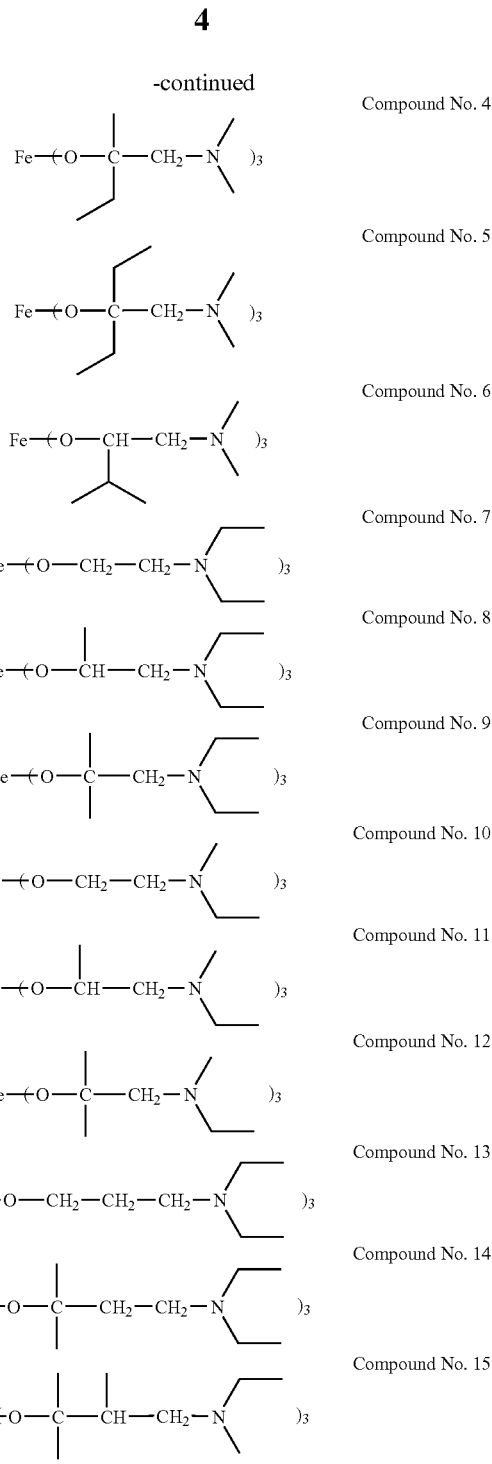

When the alkoxide compound of the present invention is used for thin film-forming processes involving a step of vaporizing a compound, preferred are compounds in which $R^1$ to $R^4$ and A in general formula (I) have a low-formula-weight because of the high vapor pressure. Specifically, $R^1$ and $R^2$ are preferably a hydrogen atom or a methyl group, $R^3$ and $R^4$ are preferably methyl groups, and A is preferably a methylene group. When the alkoxide compound of the present invention is used for thin film-forming processes involving no vaporization step such as MOD, $R^1$ to $R^4$ and A may be arbitrarily selected according to the solubility to the solvent to be used, the thin film-forming reaction, and the like.

The alkoxide compound of the present invention is free from specific limitations on its production method and can be produced by applying known methods. Common synthetic methods of alkoxide compounds using the corresponding aminoalcohol may be applied. Such synthetic methods include, for example, Method (1) in which an inorganic salt such as halides and nitrate of iron or hydrate thereof is reacted with the corresponding alcohol in the presence of a base such as sodium, sodium hydride, sodium amide, sodium hydroxide, sodium methoxide, ammonia, and amines, Method (2) in which an inorganic salt such as halides and nitrate of iron or hydrate thereof is reacted with an alkali metal alkoxide such as sodium alkoxide, lithium alkoxide, and potassium alkoxide derived from the corresponding alcohol, Method (3) in which an iron alkoxide derived from a low-molecular-weight alcohol such as iron methoxide, ethoxide, isopropoxide, and butoxide is subjected to exchange reaction with the corresponding alcohol, and Method (4) in which an inorganic salt such as halides and nitrate of iron is reacted with a derivative that gives a reactive intermediate to obtain the reactive intermediate, followed by reacting the reactive intermediate with the corresponding alcohol.

The reactive intermediate used in Method (4) above includes, for example, iron amide compounds such as tris (dialkylamino)iron and tris[bis(trimethylsilyl)amino]iron.

The thin film-forming material of the present invention contains the alkoxide compound of the present invention as a precursor of thin films. Its form (state) is accordingly selected depending on the thin film-formation process to which the thin film-forming material is applied (for example, flame deposition, sputtering, ion plating, MOD processes such as coating-thermal decomposition, sol-gel process and the like, and CVD processes including ALD). The alkoxide compound of the present invention is useful particularly for a CVD source among materials for thin film-forming processes, based on its physicochemical properties.

When the thin film-forming material of the present invention is a source material for chemical vapor deposition (CVD), its form is accordingly selected depending on the techniques for delivery/feeding and others in the CVD process to be used.

The delivery/feeding system includes a vapor delivery system in which a CVD source is vaporized by heating and/or under reduced pressure in a source reservoir and the resulting vapor is introduced to the deposition reaction chamber, optionally together with a carrier gas such as argon, nitrogen, and helium; and a liquid delivery system in which a CVD source is delivered to a vaporization chamber in a liquid or solution state, vaporized by heating and/or under reduced pressure in the vaporization chamber, and introduced to the deposition reaction chamber. In the vapor delivery system, the CVD source is the alkoxide compound of the present invention represented by general formula (I) itself, while in the liquid delivery system, the CVD source is the alkoxide compound of the present invention represented by general formula (I) itself or a solution containing the alkoxide compound dissolved in an organic solvent.

CVD processes for multi-component systems include a technique in which each component composing a CVD source is separately vaporized and fed (hereinafter, may be also called "single source feed") and a technique in which a mixed source obtained by pre-mixing a plurality of source components at a desired composition is vaporized and fed (hereinafter, may be also called "cocktail source feed"). In the cocktail source feed, the CVD source is a mixture or mixed solution containing only the alkoxide compounds of the present invention, or a mixture or mixed solution containing the alkoxide compound(s) of the present invention and (an) other precursor(s).

As the organic solvent used for the above CVD source, any common organic solvent may be used without particular limitation. Such organic solvents include alcohols such as methanol, ethanol, 2-propanol, and n-butanol; acetates such as ethyl acetate, butyl acetate, and methoxyethyl acetate; ether alcohols such as ethylene glycol monomethyl ether, ethylene glycol monoethyl ether, ethylene glycol monobutyl ether, and diethylene glycol monomethyl ether; ethers such as tetrahydrofuran, tetrahydropyran, ethylene glycol dimethyl ether, diethylene glycol dimethyl ether, triethylene glycol dimethyl ether, dibutyl ether, and dioxane; ketones such as methyl s butyl ketone, methyl isobutyl ketone, ethyl butyl ketone, dipropyl ketone, diisobutyl ketone, methyl amyl ketone, cyclohexanone, and methylcyclohexanone; hydrocarbons such as hexane, cyclohexane, methylcyclohexane, dimethylcyclohexane, ethylcyclohexane, heptane, octane, toluene, and xylene; cyanohydrocarbons such as 1-cyanopropane, 1-cyanobutane, 1-cyanohexane, cyanocyclohexane, cycanobenzene, 1,3-dicyanopropane, 1,4-dicyanobutane, 1,6-dicyanohexane, 1,4-dicyanocyclohexane, and 1,4-dicyanobenzene; pyridine and lutidine. These may be used alone or as a mixed solvent, depending on solubility of the solute, and relationships between the temperature in use and the boiling point and flash point of the solvent. When such an organic solvent is used, the total concentration of the alkoxide compound(s) of the present invention and (an)other precursor(s) is preferably 0.01 to 2.0 mole, particularly 0.05 to 1.0 mole, per liter of the organic solvent.

In CVD processes for multi-component systems, any common precursor used as a CVD source may be used as another precursor used together with the alkoxide compound of the present invention without particular limitations.

Such other precursors include compound of silicon or metal with one or more compounds selected from a group of compounds used as organic ligands such as alcohols, glycols, β-diketones, cyclopentadienes, and organic amines. The metal in another precursor includes, for example, magnesium, calcium, strontium, barium, titanium, zirconium, hafnium, vanadium, niobium, tantalum, manganese, iron, ruthenium, cobalt, rhodium, iridium, nickel, palladium, platinum, copper, silver, gold, zinc, gallium, indium, germanium, tin, lead, antimony, bismuth, yttrium, lanthanum, cerium, praseodymium, neodymium, promethium, samarium, europium, gadolinium, terbium, dysprosium, holmium, erbium, thulium, and ytterbium.

Alcohols used as the organic ligand include alkanols such as methanol, ethanol, propanol, isopropanol, butanol, 2-butanol, isobutanol, t-butanol, amyl alcohol, isoamyl alcohol, and t-amyl alcohol; ether alcohols such as 2-methoxyethanol, 2-ethoxyethanol, 2-butoxyethanol, 2-(2-methoxyethoxy) ethanol, 2-methoxy-1-methylethanol, 2-methoxy-1,1-dimethylethanol, 2-ethoxy-1,1-dimethylethanol, 2-isopropoxy-1,1-dimethylethanol, 2-butoxy-1,1-dimethylethanol, 2-(2-methoxyethoxy)-1,1-dimethylethanol, 2-propoxy-1,1-diethylethanol, 2-sec-butoxy-1,1-diethylethanol, and 3-methoxy-1,1-dimethylpropanol; dialkylaminoalcohols, which provide the alkoxide compound of the present invention; and the like.

Glycols used as the organic ligand include 1,2-ethanediol, 1,2-propanediol, 1,3-propanediol, 2,4-hexanediol, 2,2-dimethyl-1,3-propanediol, 2,2-diethyl-1,3-propanediol, 1,3-butanediol, 2,4-butanediol, 2,2-diethyl-1,3-butanediol, 2-ethyl-2-butyl-1,3-propanediol, 2,4-pentanediol, 2-methyl-1,3- propanediol, 2-methyl-2,4-pentanediol, 2,4-hexanediol, 2,4-dimethyl-2,4-pentanediol, and the like.

β-Diketones used as the organic ligand include alkyl β-diketones such as acetylacetone, hexane-2,4-dione, 5-methylhexane-2,4-dione, heptane-2,4-dione, 2-methylheptane-3,5-dione, 5-methylheptane-2,4-dione, 6-methylheptane-2,4-dione, 2,2-dimethylheptane-3,5-dione, 2,6-dimethylheptane-3,5-dione, 2,2,6-trimethylheptane-3,5-dione, 2,2,6,6-tetramethylheptane-3,5-dione, octane-2,4-dione, 2,2,6-trimethyloctane-3,5-dione, 2,6-dimethyloctane-3,5-dione, 2,9-dimethylnonane-4,6-dione, 2-methyl-6-ethyldecane-3,5-dione, and 2,2-dimethyl-6-ethyldecane-3,5-dione; fluorinated alkyl β-diketones such as 1,1,1-trifluoropentane-2,4-dione, 1,1,1-trifluoro-5,5-dimethylhexane-2,4-dione, 1,1,1,5,5,5-hexafluoropentane-2,4-dione, and 1,3-diperfluorohexylpropane-1,3-dione; ether-substituted β-diketones such as 1,1,5,5-tetramethyl-1-methoxyhexane-2,4-dione, 2,2,6,6-tetramethyl-1-methoxyheptane-3,5-dione, and 2,2,6,6-tetramethyl-1-(2-methoxyethoxy)heptane-3,5-dione; and the like.

Cyclopentadienes used as the organic ligand include cyclopentadiene, methylcyclopentadiene, ethylcyclopentadiene, propylcyclopentadiene, isopropylcyclopentadiene, butylcyclopentadiene, sec-butylcyclopentadiene, isobutylcyclopentadiene, tert-butylcyclopentadiene, dimethylcyclopentadiene, tetramethylcyclopentadiene, pentamethylcyclopentadiene, and the like.

Organic amines used as the organic ligand include methylamine, ethylamine, propylamine, isopropylamine, butylamine, sec-butylamine, tert-butylamine, isobutylamine, dimethylamine, diethylamine, dipropylamine, diisopropylamine, ethylmethylamine, propylmethylamine, isopropylmethylamine, and the like.

In the single source feed, another precursor described above preferably has a thermal and/or oxidative decomposition behavior similar to that of the alkoxide compound of the present invention. In the cocktail source feed, the preference is lack of deterioration due to chemical reaction during mixing in addition to the similarity in the thermal and/or oxidative decomposition behavior.

For example, when the alkoxide compound of the present invention is mixed with a bismuth compound as another precursor, bismuth compounds usable therein include triarylbismuth such as triphenylbismuth, tri(o-methylphenyl)bismuth, tri(m-methylphenyl)bismuth, and tri(p-methylphenyl)bismuth; trialkylbismuth such as trimethylbismuth; β-diketonato complexes such as tris(2,2,6,6-tetramethylheptane-3,5-dionato)bismuth; cyclopentadienyl complexes such as tris(cyclopentadienyl)bismuth and tris(methylcyclopentadienyl)bismuth; alkoxides derived from low-molecular-weight alcohols such as tris(t-butoxy)bismuth, tris(t-amyloxy)bismuth and tris(ethoxy)bismuth, alkoxide compounds represented by general formula shown in [Formula 5] below, trisalkoxybismuth having the same ligand as the alkoxide compound of the present invention; and the like.

[Formula 5]

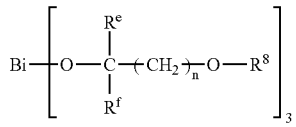

(In the formula, $R^e$ and $R^f$ each independently represent a hydrogen atom or $C_{1-3}$ alkyl group, $R^g$ represents a $C_{1-4}$ alkyl group, and n represents 1 or 2.)

The thin film-forming material of the present invention may contain a nucleophilic reagent where necessary in order to impart stability to the alkoxide compound of the present invention and (an)other precursor(s). The nucleophilic reagent includes, for example, ethylene glycol ethers such as glyme, diglyme, triglyme and tetraglyme; crown ethers such as 18-crown-6, dicyclohexyl-18-crown-6, 24-crown-8, dicyclohexyl-24-crown-8, and dibenzo-24-crown-8; polyamines such as ethylenediamine, N,N'-tetramethylethylenediamine, diethylenetriamine, triethylenetetramine, tetraethylenepentamine, pentaethylenehexamine, 1,1,4,7,7-pentamethyldiethylenetriamine, 1,1,4,7,10,10-hexamethyltriethylenetetramine, and triethoxytriethyleneamine; cyclic polyamines such as cyclam and cyclen; heterocyclic compounds such as pyridine, pyrrolidine, piperidine, morpholine, N-methylpyrrolidine, N-methylpiperidine, N-methylmorpholine, tetrahydrofuran, tetrahydropyran, 1,4-dioxane, oxazole, thiazole, and oxathiolane; β-ketoesters such as methyl acetoacetate, ethyl acetoacetate, and 2-methoxyethyl acetoacetate; and β-diketones such as acetylacetone, 2,4-hexanedione, 2,4-heptanedione, 3,5-heptanedione, and dipivaloylmethane. The amount of the nucleophilic reagent used as a stabilizer is preferably 0.1 to 10 moles, especially 1 to 4 moles, per mole of the precursor.

In the thin film-forming material of the present invention, there should be minimized contamination with substances other than components thereof including metal element impurities, halogen impurities such as chlorine-containing impurities, and organic impurities. The content of metal element impurities is preferably not more than 100 ppb and more preferably not more than 10 ppb for each element. The total content is preferably not more than 1 ppm and more preferably not more than 100 ppb. The total content of halogen impurities is preferably not more than 100 ppm, more preferably not more than 10 ppm, and most preferably not more than 1 ppm. The total content of organic impurities is preferably not more than 500 ppm, more preferably not more than 50 ppm, and most preferably not more than 10 ppm. Since water in the thin film-forming material causes particle generation in itself or during CVD processes, it is recommended that each of the metal compound, the organic solvent, and the nucleophilic reagent is dried as much as possible prior to use in order to reduce the water content thereof. In each of the metal compound, the organic solvent, and the nucleophilic reagent, the water content is preferably not more than 10 ppm and more preferably not more than 1 ppm.

In order to reduce or prevent particle contamination of thin films to be formed, in the thin film-forming material of the present invention, preferably the number of particles larger than 0.3 μm is 100 or less in 1 ml of its liquid phase, more preferably the number of particles larger than 0.2 μm is 1000 or less in 1 ml of its liquid phase, and furthermore preferably the number of particles larger than 0.2 μm is 100 or less in 1 ml of its liquid phase, when determined by particle measurement with a light-scattering submerged particle detector in its liquid phase.

In the method for forming thin films of the present invention, a thin film is formed using the thin film-forming material of the present invention by a CVD process in which vapor obtained by vaporizing the alkoxide compound of the present invention and optionally (an)other precursor(s) is introduced, optionally together with a reactive gas, on a substrate and then the decomposition and/or chemical reaction is conducted to deposit and grow a thin film on the substrate. In the method for forming thin films of the present invention, as the source delivery/feeding systems, deposition methods, formation conditions, production apparatuses, and the like, there may be employed common conditions, methods, and the like without particular limitations.

The reactive gas optionally used includes, for example, as oxidants, oxygen, ozone, nitrogen dioxide, nitrogen monoxide, steam, hydrogen peroxide, formic acid, acetic acid, acetic anhydride, and the like; as a reductant, hydrogen; and as nitriding agents, organic amines such as monoalkylamines, dialkylamines, trialkylamines, and alkylenediamines, hydrazine, ammonia, and the like.

The delivery/feeding system includes the vapor delivery system, liquid delivery system, single source feed, cocktail source feed, and the like.

The deposition method includes thermal CVD in which a source gas or a source gas and a reactive gas is/are reacted by only heating to deposit a thin film, plasma CVD using heat and plasma, light CVD using heat and light, light-plasma CVD using heat, light, and plasma, and ALD (Atomic Layer Deposition) in which the deposition reaction of CVD is divided into elementary steps to conduct stepwise deposition at a molecular level.

The formation conditions include the reaction temperature (substrate temperature), reaction pressure, deposition rate, and the like. The reaction temperature is preferably 160° C. or higher at which the alkoxide compound of the present invention is sufficiently reactive, and more preferably 250 to 800° C. The preferred reaction pressure is atmospheric pressure to 10 Pa for thermal CVD and light CVD, and 10 to 2000 Pa when using plasma. The deposition rate can be controlled by adjusting the source feed conditions (vaporization temperature and vaporization pressure), reaction 25 temperature, and reaction pressure. Since excessively high deposition rates may result in deteriorating the properties of the resulting thin film and too low deposition rates may cause a problem in productivity, the deposition rate is preferably 0.5 to 5000 nm/min and more preferably 1 to 1000 nm/min. In ALD, the number of cycles is controlled so as to obtain a desired film thickness. The thickness of thin film formed using the thin film-forming material of the present invention is selected accordingly depending on the application; however, it is typically 1 to 10000 nm and preferably 5 to 1000 nm.

In the method for forming thin films of the present invention, after deposition of a thin film, annealing may be performed under an inert atmosphere, an oxidative atmosphere, or a reducing atmosphere in order to attain more favorable electric properties, and a reflow step may be employed if bump embedding is required. In this case, the temperature is typically 400 to 1200° C. and preferably 500 to 800° C.

By the method for forming thin films of the present invention using the thin film-forming material of the present invention, there can be formed a desired type of thin film such as oxide ceramic, nitride ceramic, and glass by appropriately selecting the precursor(s) of (an)other component(s), the reactive gas, and the formation conditions. The composition of a thin film to be formed includes, for example, iron, iron-bismuth composite oxide, iron oxide, iron carbide, iron nitride, iron-titanium composite oxide, iron-zirconium composite oxide, iron-aluminum composite oxide, iron-rare earth element composite oxide, iron-bismuth-titanium composite oxide, and the like. The alkoxide compound of the present invention is particularly suitable to prepare a thin film-forming material for forming thin films of iron-bismuth composite oxide by mixing with a bismuth compound as another precursor.

The application of these thin films includes electronic component members such as high dielectric capacitor films, gate insulating films, gate films, ferroelectric capacitor films, condenser films, and barrier films; optical glass members such as optical fibers, light guides, optical amplifiers, optical switches; magnetic bodies, piezoelectric elements, electronic devices, sensors, and the like.

EXAMPLES

Hereinafter, the present invention will be further detailed with reference to Examples, Evaluation Examples, etc. However, the present invention is by no means limited by Examples or the like below.

Example 1

Production of Compound No. 3

In 50 ml of anhydrous tetrahydrofuran was dissolved 13.52 g (0.083 mol) of iron (III) chloride to prepare a solution, which was called Solution-A. Fifty milliliters of anhydrous tetrahydrofuran and 44 g (0.375 mol) of 1-dimethylamino-2-methyl-2-propanol were mixed, and 5.75 g of sodium metal was added and dissolved herein with heating and stirring. This solution was added dropwise to Solution-A, and the reaction was conducted at 65° C. for 20 hours with stirring. After the reaction, tetrahydrofuran was distilled off, 200 ml of anhydrous hexane was added to the residue, and the mixture was filtered. After hexane was evaporated from the filtrate, the concentrate was vacuum-distilled. When the pressure was 0.3 Torr, the bath temperature was 130° C., and the column-top temperature was 92° C., 14.1 g (yield: 42%) of red-brown liquid was obtained. The resulting liquid was confirmed to be the desired product, Compound No. 3. The analytical data of the resulting liquid are shown below.

(Analytical Data)
(1) Metal Element Analysis (ICP-AES)
  Iron; 13.7 mass % (Theoretical value: 13.8%)
(2) CHN Analysis (Yanaco MTA-6 model CHN Analyzer)
  Carbon: 53.4% (Theoretical value: 53.5%)
  Hydrogen: 10.4% (Theoretical value: 10.47%)
  Nitrogen: 10.4% (Theoretical value: 10.39%)
(3) TG-DTA (Ar Flow rate: 100 ml/min, Heating rate: 10° C./min, Sample weight: 8.919 mg)
  Temperature at 50% mass reduction: 216° C.

Evaluation Example 1

Vapor Pressure of Iron Alkoxide Compound

The volatility was evaluated for Compound No. 3 obtained in Example 1 above and Comparative Compound No. 1 shown in [Formula 6] below based on vapor pressure measurements. The vapor pressures were determined as follows: the vapor temperature in the vicinity of a liquid surface was measured while the system pressure was kept constant; the vapor temperatures were measured at three or four different system pressures, and a vapor pressure equation was derived from a Clausius-Clapeyron plot to calculate the vapor pressures P (Torr) at 150° C. and 200° C. . The results are shown in Table 1.

TABLE 1

| Metal compound | Vapor pressure equation | Vapor pressure P at 150° C. (Torr) | Vapor pressure P at 200° C. (Torr) |
|---|---|---|---|
| Compound No. 3 | Log P (Torr) = 9.52 − 3786/T (K) | 3.71 | 32.8 |
| Comparative Compound No. 1 | Log P (Torr) = 13.8 − 311/T (K) | 0.078 | 2.897 |

[Formula 6]

Comparative Compound No. 1

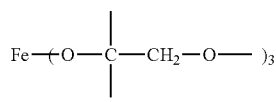

$$Fe{+}O{-}\overset{|}{\underset{|}{C}}{-}CH_2{-}O{-})_3$$

The results of Table 1 shows that Compound No. 3, which is the alkoxide compound of the present invention, has a higher vapor pressure than Comparative Compound No. 1, thereby enabling film formation even at relatively low temperatures, confirming that this compound is suitable as an iron precursor used in thin film-forming processes involving vaporization step such as CVD.

Evaluation Example 2

Volatility Evaluation of Iron Alkoxide Compound

The thermal behaviors of Compound No. 3 and Comparative Compound No. 1 were examined by TG-DTA under the same conditions as those in Example 1. The results are shown in Table 2. Here, the sample weight of Comparative Compound No. 1 was 6.772 mg.

TABLE 2

| Metal compound | Temperature at 50%-mass reduction | Residue at 300° C. | Remarks |
|---|---|---|---|
| Compound No. 3 | 221.1° C. | 1.1 mass % | The mass decreased due to volatilization |
| Comparative Compound No. 1 | 270.5° C. | 1.4 mass % | The mass decreased due to volatilization |

Table 2 shows that Compound No. 3 is more volatile than Comparative Compound No. 1 in spite of a higher molecular weight, and hence suitable as an iron precursor used in thin film-forming processes involving vaporization step such as CVD.

Example 2

Method for Forming Thin Films

Ethylcyclohexane was dried with sodium wire and then purified by distillation under an argon flow with discarding 10 mass % as the pre-distillate and 10 mass % as the residue to obtain the solvent with a water content less than 1 ppm. To 500 ml of this solvent were added 0.2 mol of Compound No. 2 and 0.2 mol of tris(1-methoxy-2-methyl-2-propoxy)bismuth under an argon atmosphere to obtain an iron-bismuth cocktail source. With the CVD apparatus shown in FIG. 1, an iron-bismuth composite oxide thin film was formed on a silicon wafer under the following conditions using the cocktail source prepared above. The film thickness and composition were measured for the formed thin film by fluorescent X-ray analysis. The results are shown below.

(Conditions)

Vaporization chamber temperature: 170° C., Source feed rate: 20 mg/min, Reaction pressure: 500 Pa, Reaction time: 30 min, Substrate temperature: 380° C., Carrier Ar: 700 sccm, Oxygen gas: 700 sccm, Film forming time: 15 min, Annealing after deposition: 10 min under oxygen at a flow rate of 100 sccm (Results)

Film thickness: 300 nm, A peak assignable to $BiFeO_3$ was observed.

Composition ratio (molar ratio): Fe/Bi=1

Comparative Example 1

Ethylcyclohexane was dried with sodium wire and then purified by distillation under an argon flow with discarding 10 mass % as the pre-distillate and 10 mass % as the residue to obtain the solvent with a water content less than 1 ppm. To 500 ml of this solvent were added 0.2 mol of tris(1-methoxy-2-methyl-2-propoxy)iron and 0.2 mol of tris(1-methoxy-2-methyl-2-propoxy)bismuth under an argon atmosphere to obtain a comparative iron-bismuth cocktail source. With the CVD apparatus shown in FIG. 1, an iron-bismuth composite oxide thin film was formed on a silicon wafer under the following conditions using the cocktail source prepared above. The thickness and composition of the thin film prepared were measured similarly to Example 2. The results are shown below.

(Conditions)

Vaporization chamber temperature: 230° C., Source feed rate: 20 mg/min, Reaction pressure: 500 Pa, Reaction time: 30 min, Substrate temperature: 380° C., Carrier Ar: 700 sccm, Oxygen gas: 700 sccm, Annealing after deposition: 10 min under oxygen at a flow rate of 100 sccm (Results)

Film thickness: 200 nm

Composition ratio (molar ratio): Fe/Bi=0.8

In Example 2, the ratio Fe/Bi in the thin film-forming material well coincides with the ratio Fe/Bi in the resulting thin film. In contrast, in Comparative Example 1, the ratio Fe/Bi in the thin film-forming material does not coincide with the ratio Fe/Bi in the resulting thin film. This fact means that the alkoxide compound of the present invention enables excellent control of the thin film composition.

INDUSTRIAL AVAILABILITY

The present invention can provide an iron alkoxide compound that can be delivered in a liquid state and is easily vaporized due to its high vapor pressure. The iron alkoxide compound is suitable as a precursor used for forming thin films by CVD or the like. Further, when the thin film-forming material of the present invention containing the alkoxide compound of the present invention is used, thin films can be produced with excellent composition controllability, which has remarkable effects particularly in forming multi-component thin films by CVD.

The invention claimed is:

1. An alkoxide compound represented by general formula (I) below:

[Formula 1]

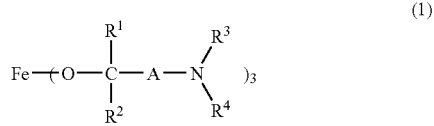

(1)

wherein $R^1$ and $R^2$ each independently represent a hydrogen atom or alkyl group having 1 to 4 carbon atoms, $R^3$ and $R^4$ each represent an alkyl group having 1 to 4 carbon atoms, and A represents an alkanediyl group having 1 to 8 carbon atoms.

2. The alkoxide compound according to claim 1, wherein A in general formula (I) is a methylene group.

3. The alkoxide compound according to claim 1, wherein $R^1$ and $R^2$ in general formula (I) are each independently a hydrogen atom or a methyl group.

4. A thin film-forming material comprising the alkoxide compound according to claim 1.

5. A material for forming thin films of iron-bismuth composite oxide comprising the alkoxide compound according to claim 1 and a bismuth compound as another precursor.

6. A method for forming thin films in which vapor containing the alkoxide compound obtained by vaporizing the thin film-forming material according to claim 4 is introduced on a substrate, followed by subjecting to decomposition and/or chemical reaction to form a thin film on the substrate.

7. The alkoxide compound according to claim 2, wherein $R^1$ and $R^2$ in general formula (I) are each independently a hydrogen atom or a methyl group.

8. A thin film-forming material comprising the alkoxide compound according to claim 2.

9. A thin film-forming material comprising the alkoxide compound according to claim 3.

10. A material for forming thin films of iron-bismuth composite oxide comprising the alkoxide compound according to claim 2 and a bismuth compound as another precursor.

11. A material for forming thin films of iron-bismuth composite oxide comprising the alkoxide compound according to claim 3 and a bismuth compound as another precursor.

12. A material for forming thin films of iron-bismuth composite oxide comprising the alkoxide compound according to claim 4 and a bismuth compound as another precursor.

13. A method for forming thin films in which vapor containing the alkoxide compound obtained by vaporizing the thin film-forming material according to claim 5 is introduced on a substrate, followed by subjecting to decomposition and/or chemical reaction to form a thin film on the substrate.

* * * * *